United States Patent [19]
Montana et al.

[11] Patent Number: 5,853,623
[45] Date of Patent: Dec. 29, 1998

[54] PEPTIDYL COMPOUNDS AND THEIR THERAPEUTIC USE AS INHIBITORS OF METALLOPROTEINASES

[75] Inventors: John Montana; David Alan Owen; Jonathan Dickens; Andrew Douglas Baxter, all of Cambridge, United Kingdom

[73] Assignee: Chiroscience Limited, United Kingdom

[21] Appl. No.: 644,383

[22] Filed: May 10, 1996

Related U.S. Application Data

[63] Continuation of PCT/GB94/02471 Nov. 10, 1994.

[30] Foreign Application Priority Data

Nov. 10, 1993 [GB] United Kingdom .................. 9323165

[51] Int. Cl.⁶ ........................... C07K 5/062; A61K 38/55
[52] U.S. Cl. .................... 260/998.2; 260/998.21; 530/868; 514/19
[58] Field of Search ........................ 260/998.2, 998.21; 530/868; 514/2, 19

[56] References Cited

U.S. PATENT DOCUMENTS 5,144,043  9/1992  Dean et al. .............................. 548/548

FOREIGN PATENT DOCUMENTS 0273689  7/1988  European Pat. Off. .
8806890  9/1988  WIPO .
9407481  4/1994  WIPO .

OTHER PUBLICATIONS

Almquist, R.G. et al. (1991) "Development of peptidomimetric inhibitors of a newly isolated atrial peptide–degrading enzyme" Peptides Chemistry and Biology, Proceedings of the Twelfth American Peptide Symposium, Jun. 16–21, 1991, Cambridge, MA, USA.

Bormans, G. et al. (1993) "Synthesis and Labelling Characteristics of $^{99m}$Tc–Mercaptoacetyltripeptides" J. Labelled Compd. Radiopharm. 33(11):1065–1078.

*Primary Examiner*—Nathan M. Nutter
*Attorney, Agent, or Firm*—Saliwanchik, Lloyd & Saliwanchik

[57] ABSTRACT

The present invention concerns novel mercaptoalkylpeptidyl compounds of formula (I) which are useful inhibitors of matrix metalloproteinase and/or TNF-mediated diseases including degenerative diseases and certain cancers. The invention also concerns methods of treating patients suffering from disorders or diseases which can be attributed to or are associated with matrix metalloproteinase or TNF activity.

10 Claims, No Drawings

PEPTIDYL COMPOUNDS AND THEIR THERAPEUTIC USE AS INHIBITORS OF METALLOPROTEINASES

CROSS-REFERENCE TO A RELATED APPLICATION

This application is a continuation of international application PCT/GB94/02471 which designated the United States, with an international filing date of Nov. 10, 1994.

FIELD OF THE INVENTION

This invention relates to a novel class of peptidyl derivatives, to processes for their preparation, and to their use in medicine.

BACKGROUND OF THE INVENTION

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least three groups of metalloproteinases. These are the collagenases (interstitial collagenase, MMP-1; PMN collagenase, MMP-8), the gelatinases (gelatinase A, MMP-2, 72 kDa-gelatinase, Type IV collagenase; gelatinase B, MMP-9, 92 kDa-gelatinase, Type IV collagenase) and the stromelysins (proteoglycanase, MMP-3, stromelysin-1, transin; stromelysin-2, MMP-10; stromelysin-3, MMP-11). Normally, these catabolic enzymes are tightly regulated at the level of their synthesis and secretion and also at the level of their extracellular activity, the latter through the action of specific inhibitors, such as TIMP (tissue inhibitors of metalloproteinase), which form inactive complexes with metalloproteinases, and more general proteinase inhibitors such as $\alpha_2$-macroglobulin.

The accelerated, uncontrolled breakdown of connective tissues by metalloproteinase-catalysed resorption of the extracellular matrix is a feature of many pathological conditions such as rheumatoid arthritis, osteoarthritis, septic arthritis, corneal, epidermal or gastric ulceration; tumour metastasis or invasion; periodontal disease, proteinuria, coronary thrombosis associated with atherosclerotic plaque rupture and bone disease. Inhibitors may also be useful in preventing the pathological squaelae following a traumatic injury that could lead to a permanent disability. These compounds may also have utility as a means for birth control, by preventing ovulation or implantation. It can be expected that the pathogenesis of such diseases is likely to be modified in a beneficial manner by the administration of metalloproteinase inhibitors, and numerous compounds have been suggested for this purpose (for a general review, see Wahl et al. [1990] Ann. Rep. Med. Chem. 25:175–184, Academic Press Inc., San Diego).

A number of small peptide-like compounds which inhibit metalloproteinases have been described. Perhaps the most notable of these relate to angiotensin-converting enzyme (ACE), where such agents act to block the conversion of the decapeptide angiotensin I to angiotensin II, a potent pressor substance. Compounds of this type are described in EP-A-0012401. Also, related mercaptoamide peptidyl derivatives have shown ACE inhibitor activity in vitro and in vivo (Weller et al. [1984] Biochem. Biophys. Res. Comm. 125(1):82–89).

TNF is a cytokine which is produced initially as a cell-associated 28 kD precursor. It is released as an active, 17 kD form (Jue et al. [1990] Biochemistry 29:8371–8377) which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal heamatopoiesis in patients with these tumours.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al. [1988] J. Clin. Invest. 81:1925–1937; Miethke et al. [1992] J. Exp. Med. 175:91–98), post-ischaemic reperfusion injury, malaria (Grau et al. [1989] Immunol. Rev. 112:49–70); mycobacterial infection (Barnes et al. [1992] Infect. Imm. 60:1441–6), meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1, and hyperoxic alveolar injury.

Current clinical anti-TNF strategies involve the use of corticosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNF gene transcription (Endres, S. [1991] Immunol. 72:56–60; Schandene et al. [1992] Immunol. 76:30–34; Alegre et al. [1991] Transplantation 52:674–679; Bianco et al. [1991] Blood 78:1205–1221). Thalidomide has also been shown to inhibit TNF production by leucocytes (Sampajo et al. [1991] J. Exp. Med. 173:699–703). In experimental settings, anti-TNF monoclonal antibodies, soluble TNF receptors and soluble TNF receptor/immunoadhesins have been shown to specifically inhibit the effects of TNF action (Bagby et al. [1991] J. Infect. Dis. 163:83–88; Charpentier et al. [1991] Presse-med. 20:2009–2011; Silva et al. [1990] J. Infect. Dis. 162:421–427; Franks et al. [1991] Infect. Immun. 59:2609–2614; Tracey et al. [1987] Nature 330:662–664; Fischer et al. [1992] PNAS USA in press; Lesslauer et al. [1991] Eur. J. Immunol. 21:2883–2886; Ashkenazi et al. [1991] PNAS USA 88:10535–10539).

It has recently been shown that the effects of TNF are mediated by two peptides, TNF-α and TNF-β. Although these peptides have only 30% homology with each other, they activate the same receptors and are encoded by immediately adjacent genes. As used herein, the term tumour necrosis factor or TNF therefore means tumour necrosis factor α and peptides having a high degrees of sequence homology with, or substantially similar physiological effects to, TNF-α, for example TNF-β.

Compounds which have the property of inhibiting the action of metalloproteinases involved in connective tissue breakdown such as collagenase, stromelysin and gelatinase have been shown to inhibit the release of TNF both in vitro and in vivo (Gearing et al. [1994] Nature 370:555–557;

McGeehan et al. [1994] *Nature* 370:558–561; WO93/20047). All of these reported inhibitors contain a hydroxamic acid zinc binding group.

Compounds that inhibit collagenase are disclosed in U.S. Pat. No. 4,511,504 issued Apr. 16, 1985 and U.S. Pat. No. 4,568,666, issued Feb. 4, 1986. Compounds of related structure that are claimed to inhibit stromelysin (proteoglycanase) are described in U.S. Pat. No. 4,771,037, issued Sep. 13, 1988.

Stromelysin and collagenase inhibitors may have utility in preventing articular cartilage damage associated with septic arthritis. Bacterial infections of the joints can elicit an inflammatory response that may then be perpetuated beyond what is needed for removal of the infective agent, resulting in permanent damage to structural components. Bacterial agents have been used in animal models to elicit an arthritic response with the appearance of proteolytic activities. See Case et al. (1989) *J. Clin. Invest.* 84:1731–40 and Williams et al. [1990] *Arth. Rheum.* 33:533–41.

Inhibitors of stromelysin, collagenase and gelatinase may be useful to control tumour metastasis, optionally in combination with current chemotherapy and/or radiation. See Matrisian et al. (1986) *PNAS USA* 83:9413–7; Wilhelm et al. (1987) *PNAS USA* 84:6725–29; Werb et al. (1989) *J. Cell Biol.* 109:872–889; Liotta et al. (1983) *Lab. Invest.* 49:636–649; and Reich et al. (1988) *In Metatasis*, Ciba Foundation Symposium, Wiley, Chicester, pp. 193–210.

Secreted proteinases such as stromelysin, collagenase and gelatinase play an important role in processes involved in the movement of cells during metastasic tumour invasion. Indeed, there is also evidence that the matrix metalloproteinases are over-expressed in certain metastatic tumour cell lines. In this context, the enzyme functions to penetrate underlying basement membranes and allow the tumour cell to escape from the site of primary tumour formation and enter the circulation. After adhering to blood vessel walls, the tumour cells use these same metalloproteinases to pierce underlying basement membranes and penetrate other tissues, thereby leading to tumour metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts derived from inflamed gingiva (Uitto et al. [1981] *J. Periodontal Res.* 16:417–424). Enzyme levels have been correlated to the severity of gum disease (Overall et al. [1987] *J. Periodontal Res.* 22:81–88).

Proteolytic processes have also been observed in the ulceration of the cornea following alkali burns (Brown et al. [1969] *Arch. Opthalmol.* 81:370–373). Mercapto-containing peptides do inhibit the collagenase isolated from alkali-burned rabbit cornea (Burns [1989] *Invest. Opthalmol.* 30:1569–1575). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine (Baricos et al. [1989] *Biochem. J.* 254:609–612). Proteinuria, a result of glomerular disease, is excess protein in the urine caused by increased permeability of the GBM to plasma proteins. The underlying causes of the increased GBM permeability are unknown, but proteinases including stromelysin may play an important role in glomerular diseases. Inhibition of this enzyme may alleviate the proteinura associated with kidney malfunction.

Inhibition of stromelysin activity may prevent the rupturing of atherosclerotic plaques, leading to coronary thrombosis. The tearing or rupture of atherosclerotic plaques is the most common event initiating coronary thrombosis. Destabilisation and degradation of the connective tissue matrix surrounding these plaques by proteolytic enzymes or cytokines released by infiltrating inflammatory cells has been proposed as a cause of plaque fissuring. Such tearing of these plaques can cause an acute thrombolytic event, as blood rapidly flows out of the blood vessel. High levels of stromelysin RNA message have been found to be localised to individual cells in atherosclerotic plaques removed from heart transplant patients at the time of surgery (Henney et al. [1991] *PNAS USA* 88:8154–8158). Inhibition of stromelysin by these compounds may aid in preventing or delaying the degradation of the connective tissue matrix that stabilises the atherosclerotic plaques, thereby preventing events leading to acute coronary thrombosis.

Specific inhibitors of stromelysin and collagenase may be useful as birth control agents. There is evidence that expression of metalloproteinases, including stromelysin and collagenase, is observed in unfertilised eggs and zygotes and at further cleavage stages, and increased at the blastocyst stage of fetal development and with endoderm differentiation (Brenner et al. [1989] *Genes & Develop.* 3:848–59). By analogy to tumour invasion, a blastocyst may express metalloproteinases in order to penetrate the extracellular matrix of the uterine wall during implantation. Inhibition of stromelysin and collagenase during these early development processes should presumably prevent normal embryonic development and/or implantation in the uterus. Such intervention would constitute a method of birth control. In addition, there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation (Woessner et al. [1989] *Steroids* 54:491–499). There may also be a role for stromelysin activity during ovulation (Too et al. [1984] *Endoctin.* 115:1043–1050).

Collagenolytic and stromelysin activities have also been observed in dystrophic epidermolysis bullosa (Kronberger et al. [1982] *J. Invest. Dermatol.* 79:208–211; Sawamura et al. [1991] *Biochem. Biophys. Res. Commun.* 184:1003–8). Inhibition of metalloendoproteinases should limit the rapid destruction of connective components of the skin.

In addition to extracellular matrix comprising structural components, stromelysin can degrade other in vivo substrates including $\alpha_1$-proteinase inhibitor, and may therefore influence the activities of other proteinases such as elastase (Winyard et al. [1991] *FEBS Letts.* 279(1):91–94). Inhibition of the matrix metalloendoproteinases may potentiate the antiproteinase activity of these endogenous inhibitors.

From recent publications it is evident that several new enzymes of the MMP family have been identified, some of which may be important in disease. Collagenase 3, an enzyme unique to breast carcinoma cells, may have utility in breast cancer (Freije et al. [1994] *J. Biol. Chem.* 269(24): 16766–16773). MT-MMP, another member of the MMP family, has been shown to be a key enzyme in the activation of gelatinase A (Sato et al. [1994] *Nature* 370:61–65). Gelatinase A is an important enzyme in the growth and metastasis of tumours (such as defined above).

The degradation of β-Amyloid Precusor Protein (APP) has been shown to generate amyloid plaques, a major constituent of the senile plaques, found in patients with Alzheimers Disease (AD). Two recent publications have identified metalloproteinase enzymes that cleave APP to the amyloid plaque (Abraham et al. [1994] *Biochemistry* 33:192–199; Huber et al. [1994] *Biochem. Biophys. Res. Comm.* 201(1):45–53).

As will be appreciated by those of skill in the art, the significant proportion of homology between these new enzymes and other MMPs leads to the possibility that a compound that inhibits one enzyme may to some degree inhibit these new enzymes. Therefore, inhibitors encompassed in this invention may be useful in the diseases in which these new enzymes are implicated.

An object behind the present invention was to provide compounds which substantially inhibit the release of TNF from cells, and which therefore may be used in the treatment of conditions mediated by TNF. Such uses include, but are not limited to, the treatment of inflammation, fever, cardiovascular effects, haemorrhage, coagulation and acute phase response, cachexia and anorexia, acute infections, shock states, graft versus host reactions and autoimmune disease.

Another object behind this invention was to provide compounds which, possibly in addition to inhibiting TNF release, also inhibit the action of MMPs, and hence may be used in the treatment of patients who suffer from conditions mediated by TNF and/or MMPs.

BRIEF SUMMARY OF THE INVENTION

The invention encompasses novel mercaptoalkylpeptidyl compounds of formula (I) which are useful inhibitors of matrix metalloproteinase and/or TNF-mediated diseases including degenerative diseases (such as defined above) and certain cancers.

According to one aspect of the invention, novel compounds are of general formula (I), i.e., as shown among the Formulae, below. With respect to formula (I) at least:

$R^1$ is $C_{1-6}$ alkyl, $C_{2-6}$ alkenyl, aryl, ($C_{1-6}$ alkyl)aryl or $C_{1-6}$ alkyl-$AR^9$ where A is O, $NR^9$ or $S(O)_m$, where m=0–2, and the or each $R^9$ is H, $C_{1-4}$ alkyl, aryl or ($C_{1-4}$ alkyl)aryl;

$R^2$ is H or $C_{1-6}$ alkyl;

X represents $NR^4R^5$ and either $R^4$ is H or $C_{1-6}$ alkyl optionally substituted by amino ($NH_2$), arylamino, protected amino, aryl, di($C_{1-6}$ alkyl)amino, mono($C_{1-6}$ alkyl)amino, $CO_2H$, protected carboxyl, carbamoyl, mono ($C_{1-6}$ alkyl)carbamoyl or di($C_{1-6}$ alkyl)carbamoyl, and $R^5$ is H or $C_{1-6}$ alkyl, or $NR_4R_5$ is pyrrolidino, piperidino or morpholino;

$R^3$ represents $[Alk]_nR^6$ and $R^6$ is optionally-substituted $C_{3-6}$ cycloalkyl, $C_{3-6}$ cycloalkenyl, $C_{1-6}$ alkyl, benzyl, ($C_{1-6}$ alkoxy)benzyl, benzyloxybenzyl or 3-indolylmethyl, Alk is $C_{1-6}$ alkyl or $C_{2-6}$ alkenyl and n=0 or 1;

$R^7$ is H or $R^{10}CO$ where $R^{10}$ is $C_{1-4}$ alkyl, ($C_{,1-4}$ alkyl) aryl, $C_{,3-6}$ cycloalkyl, ($C_{3-6}$ cycloalkyl)$C_{1-4}$ alkyl, $C_{2-6}$ alkenyl or ($C_{2-6}$ alkenyl)aryl; and $R^8$ is H, $C_{1-4}$ alkyl, ($C_{1-4}$ alkyl)aryl or aryl;

or a salt, solvate or hydrate thereof.

DETAILED DISCLOSURE OF THE INVENTION

It will be appreciated that the compounds according to the invention can contain one or more asymmetrically-substituted carbon atoms, for example those marked with an asterisk in formula (I). The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric center to represent the possibility of R- and S-configurations, the < line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including, for example, methyl, ethyl, propyl, isopropyl, butyl, t-butyl, pentyl hexyl. Thus, for example, $[Alk]_nR^6$ may be t-butyl.

The term "$C_{1-4}$ alkyl" refers to a straight or branched chain alkyl moiety having from one to four carbon atoms, including, for example, methyl, ethyl, propyl, isopropyl, butyl and t-butyl.

The term "$C_{2-6}$ alkenyl" refers to a straight or branched chain alkyl moiety having two to six carbon atoms and having in addition one double bond, of either E or Z stereochemistry where applicable. This term includes, for example, vinyl, 1-propenyl, 1- and 2-butenyl, and 2-methyl-2-propenyl.

The term "cyclo($C_{3-6}$)alkyl" refers to a saturated alicyclic moiety having from three to six carbon atoms and includes, for example, cyclopropyl, cyclobutyl, cyclopentyl and cyclohexyl.

The term "cyclo($C_{3-6}$)alkenyl" refers to an alicyclic moiety having from three to six carbon atoms and having in addition one double bond. This term includes, for example, cyclopentenyl and cyclohexenyl.

The term "aryl" means an optionally-substituted phenyl or naphthyl group with the substituent(s) being selected, for example, from halogen, trifluoromethyl, $C_{1-6}$ alkyl, alkoxy, phenyl and the like. The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily-cleavable ester such as the methyl, ethyl, benzyl or tert-butyl ester.

The term "alkoxy" refers to a straight chain or branched chain alkoxy group containing a maximum of six carbon atoms, such as methoxy, ethoxy, propoxy, isopropoxy, butoxy or tert-butoxy.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2R^{11}$ where $R^{11}$ may be an ethyl, benzyl, phenethyl, phenylpropyl, or $\alpha$ or $\beta$-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trmethylbenzyloxymethyl or pivaloyloxymethyl group.

Preferred compounds of the invention include those in which, independently or in any combination:

$R^1$ represents a $C_{1-4}$ alkyl or $C_{1-3}$ alkyl-OH group, for example a 2-methylpropyl (isobutyl) or 2-hydroxyethyl group;

$R^2$ represents hydrogen;

n is zero;

$R^4$ represents hydrogen or a $C_{1-3}$ alkyl group, for example a methyl group;

$R^5$ represents hydrogen or a $C_{1-3}$ alkyl group, for example a methyl group;

$R^6$ represents a benzyl or 3-indolylmethyl group;

$R^7$ represents hydrogen or the group $R^{10}CO$ where $R^{10}$ is a $C_{1-4}$ alkyl group, for example methyl;

$R^8$ represents a $C_{1-4}$ alkyl, aryl or ($C_{1-3}$ alkyl)aryl group, for example a phenyl or benzyl group;

Particularly preferred compounds according to the invention include:

N-[N-(Mercaptoacetyl)-L-leucyl]-L-phenylalanine methylamide

N-(Acetylmercaptoacyl)-L-leucyl-L-phenylalanine methylamide (RS)-2-(Acetylthio)pentanoyl-L-leucyl-L-phenylalanine N-methylamide (RS)-2-(Acetylthio)propanoyl-L-leucyl-L-phenylalanine N-methylamide (RS)-2-(Acetylthio)-3-methylbutanoyl-L-leucyl-L-phenylalanine N-methylamide (RS)-2-(Acetylthio)-2-phenylacetyl-L-leucyl-L-phenylalanine N-methylamide (RS)-2-(Acetylthio)-3-phenylpropanoyl-L-leucyl-L-phenylalanine N-methylamide (RS)-2-(Acetylthio)-4phenylbutanoyl-L-leucyl-L-phenylalanine N-methylamide N-(Acetylmercaptoacyl)-L-threonyl-L-phenylalanine methylamide N-(Acetyhnercaptoacyl)-L-leucyl-L-tryptophan methylamide (RS)-2-Mercaptopentanoyl-L-leucyl-L-phenylalanine N-methylamide (RS)-2-Mercaptopropanoyl-L-leucyl-L-phenylalanine N-methylamide (RS)-2-Mercapto-3-methylbutanoyl-L-leucyl-L-phenylalanine N-methylamide (RS)-2-Mercapto-2-phenylacetyl-L-leucyl-L-phenylalanine N-methylamide (RS)-2-Mercapto-3-phenylpropanoyl-L-leucyl-L-phenylalanine N-methylamide (RS)-2-Mercapto-4-phenylbutanoyl-L-leucyl-L-phenylalanine N-methylamide N-[N-(Mercaptoacetyl)-L-threonyl]-L-phenylalanine methylamide and N-[N-(Mercaptoacetyl)-L-leucyl]-L-tryptophan methylamide Compounds of the general formula (I) may be prepared by any suitable method known in the art and/or by the following processes, which themselves form part of the invention. It will be appreciated that where a particular stereoisomer of formula (I) is required, the synthetic processes described herein may be used with the appropriate homochiral starting material, and/or isomers may be resolved from mixtures using conventional separation techniques (e.g. HPLC).

The compounds according to the invention may be prepared by the following process. In the description and formulae below, the groups $R^1$, $R^2$, $R^3$, $R^6$, $R^7$, $R^8$, and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see Greene, T. W., and P. G. M. Wuts, *Protective Groups in Organic Synthesis*, Wiley Interscience.

A process for preparing compounds of general formula (I) comprises deprotecting (for example by hydrolysis) a compound having a general formula [II] which is formula (I) wherein $R^7$ represents a suitable protecting group (e.g. tert-butyl or acetate).

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Intermediates of general formula (II) may be prepared by coupling an acid of formula (III) wherein $R^7$ and $R^8$ are as defined above, or an active derivative thereof, with an amine of formula (IV). Active derivatives of acids of formula (III) include, for example, acid anhydrides or acid halides, such as acid chlorides.

The coupling reaction may be performed using standard conditions for amination reactions of this type. Thus, the reaction may be achieved in a solvent, for example an inert organic solvent such as an ether, e.g., a cyclic ether such as tetrahydrofuran, an amide, e.g., a substituted amide such as dimethylformamide, or a halogenated hydrocarbon such as dichloromethane at a low temperature e.g., −30° C. to ambient temperature, such as −20° C. to 0° C., optionally in the presence of a base, e.g., an organic base such as an amine, e.g., triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate, for example ethyl chloroformate, prior to reaction with the amine of formula (IV).

The amine of general formula (IV) may be prepared by coupling an acid of formula (V), or an active derivative thereof with an amine of formula (VI), followed by removal of any protecting groups.

Active derivatives of acids of formula (V) include, for example, acid anhydrides or acid halides such as acid chlorides as outlined earlier.

Amino acids and their derivatives as depicted by general formulae (V) and (VI) can be obtained in chiral or racemic form. In the chiral form they provide asymmetric building blocks for the chiral synthesis of compounds of general formula (I). Many of these derivatives can be readily obtained from commercially available starting materials using methods known to those skilled in the art (see, e.g., Bodanszk et al. [1984] *The Practice of Peptide Synthesis*, Springer Verlag, N.Y.; WO92/21360).

Compounds of general formula (II) may be prepared by nucleophilic substitution of compounds of general formula (VII) wherein $R^{14}$ represents a suitable leaving group (e.g., a halogen such as bromide, or an alkyl sulphonate ester such as methanesulphonate) with a thiol of general formula (VIII) wherein $R^7$ represents a suitable protecting group (e.g., tert butyl or acetate), using standard conditions known to those skilled in the art, as exemplified in WO90/05719.

Thiols of general formula (VIII) may be obtained from commercially available starting materials using methods known to those skilled in the art. Many thiols of general formula (VIII) are also commercially available.

Compounds of general formula (VII) may be prepared by coupling an acid of general formula (IX) wherein $R^{14}$ and $R^8$ are as defined above (or suitably protected versions thereof) or an active derivative thereof, with an amine of formula (IV) using similar coupling conditions to those described for the preparation of compounds of formula (II).

Carboxylic acids of the structures depicted in formulae (III) and (IX) can be obtained in chiral or racemic form. Many of these derivatives can be readily obtained from commercially available starting materials, using methods known to those skilled in the art (see WO90/05719).

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol, e.g., ethanol) of a compound of formula (I) wherein $R^1$ is a $C_{2-6}$ alkenyl group. A compound of formula (I) wherein $R^7$ is $R^{10}CO$ may be prepared by acylation (using a suitable acid chloride $R^{10}COCl$, in the presence of a base such as a triethylamine in a suitable solvent, such as a chlorinated solvent, e.g., dichloromethane) of a compound of formula (I) wherein $R^7$ is H.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNF release. The activity and selectivity of the compounds may be determined by use of the appropriate enzyme inhibition test, for example, as described in Example A hereinafter.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns a method of management (by which is meant treatment or prophylaxis) of disease or conditions mediated by TNF and/or MMPs in mammals, in particular in humans, which method comprises administering to the mammal an effective amount of a compound of formula (I) above, or a pharmaceutically acceptable salt thereof. For this purpose, a compound of formula (I) may be used in the preparation of an agent for the management (by which is meant treatment or prophylaxis) of diseases or conditions mediated by TNF and/or MMPs.

The disease or conditions referred to above include inflammation, fever, cardiovascular effects, haemorrhage, coagulation and acute phase response, cachexia and anorexia, acute infections, shock states, graft versus host reactions and autoimmune disease; and those involving tissue breakdown such as bone resportion, inflammatory diseases, dermatological conditions, tumour growth, angiogenesis and invasion by secondary metastases, in particular rheumatoid arthritis, osteoarthritis, periodontitis, gingivitis, corneal ulceration, tumour growth, angiogenesis and invasion by secondary metastases.

For the treatment of rheumatoid arthritis, osteoarthritis, and in diseases and indications resulting from the over-expression of matrix metalloendoproteinases such as are found in certain metastatic tumour cell lines or other diseases mediated by the matrix metalloendoproteinases or increased TNF production, the compounds of formula (I) may be administered orally, topically, parenterally, by inhalation, spray or rectally, in dosage unit formulations containing non-toxic pharmaceutically-acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs and cats, the compounds of the invention are effective in the treatment of humans.

A pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavouring agents, colouring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time-delay material such as glyceryl monostearate or glyeryl distearate may be employed. They may also be coated by the techniques described in U.S. Pat. Nos. 4,256,108; 4,166,452; and 4,265,874, to form osmotic therapeutic tablets for control release.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long-chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein. Sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of formula (I) are employed. For the purposes of this application, topical application includes the use of mouth washes and gargles.

Dosage levels of the order of from about 0.05 mg to about 140 mg per kilogram of body weight per day are useful in the treatment of the above-indicated conditions (about 2.5 mg to about 7 g per patient per day). For example, inflammation may be effectively treated by the administration of from about 0.01 to 50 mg of the compound per kilogram of body weight per day (about 0.5 mg to about 3.5 g per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following non-limiting Examples 1–23 illustrate the preparation of compounds of formula (I), using materials including the following Intermediates. Examples A to D illustrate test protocols.

In the Examples, the following abbreviations are used:

| | |
|---|---|
| DCC | Dicyclohexylcarbodiimide |
| RT | Room temperature |
| EDC | 1-(3-Dimethylaminopropyl)-3-ethylcarbodiimide hydrochloride |
| THF | Tetrahydrofuran |
| TNF-α | Tumour necrosis factor-α |
| PMA | Phorbol-13-myristate-12-acetate |
| ELISA | Enzyme-linked immunosorbent assay |

Intermediate 1

L-Phenylalanine N-methylamide

DCC (3.02 g) was added to a solution of L-phenylalanine-N-benzylcarbamate (4.00 g) and N-hydroxysuccinimide (1.69 g) in dry THF (35 ml) at 0° C. The mixture was stirred at that temperature for 16 h and filtered through Celite. To the filtrate was added aqueous methylamine (40% aq., 5 ml) and the mixture was stirred at RT for 24 h. The reaction mixture was concentrated in vacuo and the crude material (6.01 g) was dissolved in ethanol (250 ml). A suspension of 10% palladium on carbon in $H_2O$ (ca 2 ml) was added to the ethanol solution in a bomb. The mixture was stirred in the presence of hydrogen at 724 kPa (105 psi) for 18 h. The solution was filtered through Celite and the filtrate was evaporated in vacuo. The residue was partioned between 1N hydrochloric acid (110 ml) and dichloromethane (50 ml). The layers were separated and the aqueous layer was extracted with dichloromethane (50 ml). The aqueous layer was basified with 3N sodium hydroxide solution to pH ~14 and extracted with dichloromethane (3×50 ml). The latter extracts were combined, dried ($Na_2SO_4$), filtered and evaporated, to give the title compound as a colourless viscous oil which solidified under high vacuum (2.24 g).

TLC $R_f$ 0.15 (5% MeOH—$CH_2Cl_2$)

Similarly prepared was:

Intermediate 2

L-tryptophan N-methylamide

From L-tryptophan-N-benzylcarbamate (50 g) as a colourless oil (14.3 g)

TLC $R_f$ 0.30 (5% MeOH—$CH_2Cl_2$).

Intermediate 3

N-[N-(Carbobenzyloxy)-L-leucyl]-L-phenylalanine methylamide

Intermediate 1 (1.33 g), L-leucine-N-benzylcarbamate (1.98 g), N-hydroxybenzotriazole (1.21 g) and EDC (1.57 g) were stirred together in dry THF (30 ml) at 0° C. for 24 h. Water (10 ml) and dichloromethane (10 ml) was added and the organic solvent was removed in vacuo, the aqueous phase was partitioned between dilute hydrochloric acid (1N, 10 ml) and ethyl acetate (20 ml). The organic layer was separated, washed with saturated bicarbonate solution (8%, 20 ml) and brine (20 ml), dried ($Na_2SO_4$), filtered and evaporated to give an opaque gel. This was redissolved in dichloromethane and evaporated in vacuo to give the product as a colourless solid (2.78 g).

TLC $R_f$ 0.60 (EtOAc)

Similarly prepared were:

Intermediate 4

N-[N-(Carbobenzyloxy)-L-leucyl]-L-tryptophan methylamide

From Intermediate 2 (11.4 g) as a white solid (20 g)

TLC $R_f$ 0.46 (5% MeOH—$CH_2Cl_2$)

Intermediate 5

N-[N-(Carbobenzyloxy)-L-threonyl]-L-phenylalanine methylamide

From L-threonine-N-benzylcarbamate (4.3 g) as a colourless oil (7.7 g)

TLC $R_f$ 0.31 (5% MeOH—$CH_2Cl_2$)

Intermediate 6

N-(L-leucyl)-L-phenylalanine methylamide

Intermediate 3 (2.78 g) was dissolved in ethanol (140 ml) and then 10% palladium on carbon (0.5 g) (as a slurry in ca 3 ml $H_2O$) was added. The suspension was stirred under a hydrogen atmosphere for 16 h. The mixture was filtered through Celite, washing with dichloromethane (20 ml). Evaporation of the filtrate gave a colourless semi-solid which was dissolved in 1N hydrochloric acid (100 ml) and extracted with dichloromethane (3×50 ml), then basified with sodium hydroxide (3N, 50 ml) and extracted with dichloromethane (3×50 ml). The latter extracts were combined, dried ($Na_2SO_4$), filtered and evaporated to give the title compound as a colourless solid (1.66 g).

TLC $R_f$ 0.13 (5% MeOH—$CH_2Cl_2$)

Intermediate 7

N-(L-leucyl)-L-tryptophan methylamide

A solution of Intermediate 4 (2 g) in cyclohexene (50 ml) and ethanol (50 ml) was treated with 10% palladium on carbon (0.2 g). The mixture was stirred at reflux for 2 h. The solvent was removed in vacuo after filtration through Celite and the residue purified by flash column chromatography ($SiO_2$, 10% MeOH, $CH_2Cl_2$) to yield a hygroscopic colourless solid (1.05 g).

TLC $R_f$ 0.38 (10% MeOH—$CH_2Cl_2$)

Similarly prepared was:

Intermediate 8

N-(L-threonyl)-L-phenylalanine methylamide

From Intermediate 5 (6.6 g) as a white solid (3.31 g)

TLC $R_f$ 0.05 (5% MeOH—$CH_2Cl_2$)

Intermediate 9

Acetylmercaptoacetic acid

Sodium (460 mg) was added to ethanol (20 ml), then thiolacetic acid (1.50 ml) was added to the solution. After 5 min, bromoacetic acid (2.78 g) was added and the mixture was stirred at RT for 18 h. The reaction mixture was diluted with dichloromethane (60 ml) and filtered through Celite. The filtrate was evaporated to give a pale yellow oil. The crude product was dissolved in dichloromethane (10 ml), refiltered and evaporated to give the title compound as a pale yellow oil (2.84 g).

$^1$H NMR (200 MHz; $CDCl_3$; Ref TMS) 2.41 (s,3H) and 3.75 (s, 2H)

Intermediate 10

(RS)-2-Bromopentanoic acid

A solution of D,L-nor-valine (10 g) and potassium bromide (35.5 g) in aqueous sulphuric acid (1.25M, 130 ml) was treated portionwise at 0° C. with solid sodium nitrite (8.8 g) over a period of 1 h. The solution was then allowed to warm to RT and stirred for 2 h. The mixture was extracted with dichloromethane (2×100 ml), the combined extracts dried ($MgSO_4$) and evaporated in vacuo to provide the title compound (11.53 g) as a colourless oil.

TLC $R_f$ 0.60 (EtOAc)

Similarly prepared were:

Intermediate 11

(RS)-2-Bromo-3-methylbutanoic acid

From D,L-Valine (10 g) as a colourless oil (11.48 g)

TLC $R_f$ 0.54 (EtOAc)

Intermediate 12

(RS)-2-Bromo-2-phenylacetic acid

From D,L-phenylglycine (10 g) as a pale yellow oil (7.24 g)

TLC $R_f$ 0.58 (EtOAc)

Intermediate 13

(RS)-2-Bromo-3-phenylpropanoic acid

From D,L-phenylalanine (5 g) as a pale yellow oil (6.72 g)

TLC $R_f$ 0.58 (EtOAc)

Intermediate 14

(RS)-2-Bromo-4-phenylbutanoic acid

From D,L-homo-phenylalanine (970 mg) as a white solid (1.0 g)

TLC $R_f$ 0.13 (EtOAc)

Intermediate 15

(RS)-2-(Acetylthio)pentanoic acid

A solution of Intermediate 10 (3.0 g) in ethanol (50 ml) was treated with potassium thiolacetate (2.1 g) and the mixture stirred at RT overnight. The solution was evaporated in vacuo and the residue partitioned between water (30 ml) and dichloromethane (30 ml). The organic layer was washed with brine (30 ml), dried (MgSO$_4$) and evaporated in vacuo to provide the title compound (2.23 g) as a yellow oil.

TLC $R_f$ 0.55 (EtOAc)

Similarly prepared were:

Intermediate 16

(RS)-2-(Acetylthio)propanoic acid

From (RS)-2-bromopropanoic acid (1.63 g) as a yellow oil (1.38 g)

TLC $R_f$ 0.4 (5% EtOH—CHCl$_3$)

Intermediate 17

(RS)-2-(Acetylthio)-3-methylbutanoic acid

From Intermediate 11 (5 g) as a pale yellow oil (4.1 g)

TLC $R_f$ 0.5 (EtOAc)

Intermediate 18

(RS)-2-(Acetylthio)-2-phenylacetic acid

From Intermediate 12 (3.0 g) as yellow oil (1.64 g)

TLC $R_f$ 0.5 (EtOAc)

Intermediate 19

(RS)-2-(Acetylthio)-3-phenylpropanoic acid

From Intermediate 13 (2.0 g) as a yellow oil (1.41 g)

TLC $R_f$ 0.80 (EtOAc)

Intermediate 20

(RS)-2-(Acetylthio)-4-phenylbutanoic acid

From Intermediate 14 (860 mg) as a tan oil (340 mg)

TLC $R_f$ 0.35 (EtOAc)

Following are examples which illustrate procedures for practicing the invention. These examples should not be construed as limiting. All percentages are by weight and all solvent mixture proportions are by volume unless otherwise noted.

EXAMPLE 1

N-[N-(Acetylmercaptoacetal)-L-leucyl]-L-phenylalanine N-methylamide

Intermediate 6 (113 mg) and Intermediate 9 (52 mg) were dissolved in dry THF (10 ml), N-hydroxybenzotriazole (63 mg) was added followed by EDC (82 mg) and the solution was stirred at 0° C. for 16 h. The reaction mixture was concentrated in vacuo and the residue was partitioned between 1N hydrochloric acid (20 ml) and ethyl acetate (20 ml). The layers were separated and the organic phase was extracted with saturated sodium bicarbonate solution (2×20 ml) and brine (20 ml), dried (MgSO$_4$) and evaporated to give the crude product as a colourless solid (146 mg). Purification by flash column chromatography (8×1.5 cm, EtOAc as eluant, loading with CH$_2$Cl$_2$) gave the title compound as a colourless solid (110 mg).

TLC $R_f$ 0.35 (EtOAc)

$^1$H NMR (200 MHz; CDCl$_3$; Ref TMS): 0.90 (m,6H), 1.3–1.8 (m,3H), 2.4 (s,3H), 2.7 (d, 3H), 2.9–3.3 (m, 2H), 3.5 (s,2H), 4.2 (m,1H), 4.6 (m,1H), 6.1 (m,1H), 6.45 (br.d, 1H), 6.6 (br.d, 1H), 7.1–7.4 (m, 5H)

Similarly prepared were:

EXAMPLE 2

(RS)-2-(Acetylthio)pentanoyl-L-leucyl-L-phenylalanine N-methylamide

From Intermediate 15 (300 mg) and Intermediate 6 (500 mg) as a white solid (540 mg)

TLC $R_f$ 0.63 (5% MeOH—CH$_2$Cl$_2$)

C$_{23}$H$_{35}$N$_3$O$_4$S [449.6];[MH$^+$]=450;[MNa$^+$]=472.

EXAMPLE 3

(RS)-2-(Acetylthio)propanoyl-L-leucyl-L-phenylalanine N-methylamide

From Intermediate 16 (180 mg) and Intermediate 6 (355 mg) as a white solid (314 mg)

TLC $R_f$ 0.33 (EtOAc)

C$_{21}$H$_{31}$N$_3$O$_4$S [421.6]; [MH+]=422

EXAMPLE 4

(RS)-2-(Acetylthio)-3-methylbutanoyl-L-leucyl-L-phenylalanine N-methylamide

From Intermediate 17 (330 mg) and Intermediate 6 (553 mg) as a white solid (570 mg) after recrystalisation from diethyl ether TLC $R_f$ 0.36, 0.40 (diastereomers) (EtOAc)

C$_{23}$H$_{35}$N$_3$O$_4$S [449.6]; [MH$^+$]=450; [MNa$^+$]=47.2

EXAMPLE 5

(RS)-2-(Acetylthio)-2-phenylacetyl-L-leucyl-L-phenylalanine N-methylamide

From Intermediate 18 (360 mg) and Intermediate 6 (500 mg) as a white solid (660 mg)

TLC $R_f$ 0.37 (5% MeOH—CH$_2$Cl$_2$)
$C_{26}H_{33}N_3O_4S$ [483.6]; [MH$^+$]=484, [MNa$^+$]=496

EXAMPLE 6

(RS)-2-(Acetylthio)-3-phenylpropanoyl-L-leucyl-L-phenylalanine N-methylamide

From Intermediate 19 (420 mg) and Intermediate 6 (553 mg) as a white solid (410 mg) after recrystalisation from diethyl ether TLC $R_f$ 0.36, 0.43 (diastereomers) (EtOAc)
$C_{27}H_{35}N_3O_4S$ [497.7]; [MH$^+$]=498; [MNa$^+$]=520

EXAMPLE 7

(RS)-2-(Acetylthio)-4-phenylbutanoyl-L-leucyl-L-phenylalanine N-methylamide

From Intermediate 20 (350 mg) and Intermediate 6 (500 mg) as a white solid (640 mg)
TLC $R_f$ 0.39 (5% MeOH—CH$_2$Cl$_2$)
$C_{28}H_{37}N_3O_4S$ [511.7]; [MH$^+$]=512; [MNa$^+$]=534

EXAMPLE 8

N-[N-(Acetylmercaptoacetyl)-L-threonyl]-L-phenylalanine methylamide

From Intermediate 9 (0.48 g) and Intermediate 8 (1.0 g) as a white solid (0.83 g)
TLC $R_f$ 0.35 (7% MeOH—CH$_2$—Cl$_2$)
$^1$H NMR (200 MHz: CDCl$_3$+CD$_3$OD:Ref TMS).1.1(d, 3H), 2.4 (s,3H), 2.7(d,3H),3.1(m,2H), 3.6(d,2H), 4.2(m,2H), 4.6(m,1H), 7.2(m,5H).

EXAMPLE 9

N-[N-(Acetylmercaptoacetyl)-L-leucyl]-L-tryptophan methylamide

From Intermediate 9 (220 mg) and Intermediate 7 (500 mg) as a white solid (590 mg)
TLC $R_f$ 0.22 (EtOAc)
$C_{22}H_{30}N_4O_4S$ [446.6]; [MH$^+$]=447

EXAMPLE 10

N-[N-(Mercaptoacetyl)-L-leucyl]-L-phenylalanine methylamide

Example 1 (16 mg) was stirred with saturated ammonium hydroxide solution (200 ml) and methanol (400 ml) at room temperature under nitrogen for 2 h. The solution was acidified with dilute hydrochloric acid (2N) and the mixture was extracted with dichloromethane (3×40 ml). The combined organic fractions were dried (Na$_2$SO$_4$), filtered and evaporated to give the crude product as a colourless solid (14.2 mg). Purification by flash column chromatography (1.5×10 cm; EtOAc as eluant; loading with CH$_2$Cl$_2$) gave the title compound as a colourless solid (6.0 mg).

TLC $R_f$ 0.23 (EtOAc).
$^1$H NMR (200 MHz; CDCl$_3$; Ref TMS): 0.90 (d, 3H), 0.93 (d, 3H), 1.48–1.71 (m, 3H), 1.86 (t, 1H), 2.74 (d, 3H) 3.02–3.17 (m, 4H), 4.40 (m, 1H) 4.6 (q, 1H), 6.03 (br m, 1H), 6.82 (br d, 1H), 6.99 (br d, 1H), and 7.12–7.37 (m, 5H).
Similarly prepared were:

EXAMPLE 11

(RS)-3-Mercaptopentanoyl-L-leucyl-L-phenylalanine N-methylamide

From Example 2 (200 mg) as a white solid (180 mg)
TLC $R_f$ 0.37 (5% MeOH—CH$_2$Cl$_2$)
$C_{21}H_{33}N_3O_3S$ [407.6]; [MH$^+$]=408; [MNa$^+$]=430

EXAMPLE 12

(RS)-2-Mercapto-3-methylbutanoyl-L-leucyl-L-phenylalanine N-methylamide

From Example 4 (200 mg) as a white solid (190 mg)
TLC $R_f$ 0.41 (5% MeOH—CH$_2$Cl$_2$)
$C_{25}H_{33}N_3O_3S$ [407.6]; [MH$^+$]=408, [MNa$^+$]=430

EXAMPLE 13

(RS)-2-Mercapto-2-phenylacetyl-L-leucyl-L-phenylalanine N-methylamide

From Example 5 (200 mg) as a white solid (173 mg)
TLC $R_f$ 0.28 [5% MeOH—CH$_2$Cl$_2$]
$C_{24}H_{31}N_3O_3S$[441.6]; [MH$^+$]=442, [MNa$^+$]=464

EXAMPLE 14

(RS)-2-Mercapto-3-phenylpropanoyl-L-leucyl-L-phenylalanine N-methylamide

From Example 6 (202 mg) as a white solid (185 mg)
TLC $R_f$ 0.28 (5% MeOH—CH$_2$Cl$_2$)
$C_{25}H_{33}N_3O_3S$ [455.6]; [MH$^+$]=456

EXAMPLE 15

(RS)-2-Mercapto-4-phenylbutanoyl-L-leucyl-L-phenylalanine N-methylamide

From Example 7 (150 mg) as a white solid (138 mg)
TLC $R_f$ 0.20 (5% MeOH—CH$_2$Cl$_2$)
$C_{26}H_{35}N_3O_3S$ [469.6]; [MH$^+$]=470, [MNa$^+$]=492

EXAMPLE 16

N-[N-(Mercaptoacetyl)-L-leucyl]-L-tryptophan methylamide

From Example 9 (120 mg) as a white solid (100 mg)
TLC $R_f$ 0.12 (5% MeOH—CH$_2$Cl$_2$)
$C_{20}H28N_3O_3S$ [390.5]; [MH$^+$]=391

EXAMPLE 17

N-[N-(Mercaptoacetyl)-L-threonyl]-L-phenylalanine methylamide

From Example 8 (0.3 g) as a white solid (0.09 g)
TLC $R_f$ 0.09 (5% MeOH—CH$_2$Cl$_2$)
$^1$H NMR (200 MHz.DMSO) 1.0 (d, 3H), 2.5 (d, 3H), 2.8 (m, 3H), 3.0 (d.d, 1H), 3.2 (m, 2H), 3.9 (m, 1H), 4.2 (d.d, 1H), 4.4 (m, 1H), 5.0 (d,1H), 7.2 (m, 5H), 7.8 (m, 1H), 8.0 (m, 2H)

EXAMPLE 18

(RS)-2-Mercaptopropanoyl-L-leucyl-L-phenylalanine N-methylamide

A solution of sodium methoxide (10 mg) in methanol (1.5 ml) was treated with Example 3 (56 mg, 0.133 mmol) and the mixture stirred at room temperature for 1 hour. The solvent was evaporated in vacuo and the residue partitioned between dichloromethane (15 ml) and 2M hydrochloric acid (10 ml). The aqueous portion was re-extracted with dichloromethane (10 ml) and the combined extracts dried (Na$_2$SO$_4$) and evaporated in vacuo to provide a white solid. Purification by column chromatography (SiO$_2$, 3% methanol, dichloromethane) provided the title compound (13 mg) as a white solid.

C$_{19}$H$_{29}$N$_3$O$_3$S [379.5]; MS [MH$^+$]=380

TLC R$_f$ 0.32 (5% MeOH—CH$_2$Cl$_2$)

EXAMPLES 19–23

Five further compounds that may be made by procedures analogous to those described above are those of formula (I) wherein R$^2$=R$^4$=R$^8$=H, R$^5$=CH$_3$, R$^6$=- - -benzyl, R$^7$=CH$_3$CO, n=0 and;

R$^1$=◂CH$_2$SCH$_3$ (Ex. 19);
R$^1$=◂CH$_2$SOCH$_3$ (Ex. 20);
R$^1$=◂CH$_2$SO$_2$CH$_3$ (Ex. 21);
R$^1$=◂CH$_2$OH (Ex. 22);
R$^1$=◂CH$_2$CH$_2$OH (Ex. 23).

EXAMPLE A
Collagenase inhibition activity

The potency of compounds of general formula (I) to act as inhibitors of collagenase was determined by the procedure of Cawston and Barrett ([1979] *Anal. Biochem.* 99:340–345) whereby a 1 mM solution of the inhibitor being tested or dilutions thereof was incubated at 37° C. for 16 hours with collagen and collagenase (buffered with 50 mM Tris, pH 7.6, containing 5 mM CaCl$_2$, 0.05% Brij 35, 60 mM NaCl and 0.02% NaN$_3$). The collagen was acetylated $^3$H or $^{14}$C—collagen prepared by the method of Cawston and Murphy ([1981] *Methods in Enzymology* 80:711). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1mM inhibitor, or a dilution thereof, was compared to activity in a control devoid of inhibitor and the results reported as that inhibitor concentration effecting 50% inhibition of the collagenase (IC$_{50}$).

EXAMPLE B
Stromelysin inhibition activity

The potency of compounds of general formula (I) to act as inhibitors of stromelysin was determined using the procedure of Cawston et al. ([1981] *Biochem. J.* 195:159–165), whereby a 1 mM solution of the inhibitor being tested or dilutions thereof was incubated at 37° C. for 16 hours with stromelysin and $^{14}$C-acetylated casein (buffered with 50 mM Tris, pH 7.6, containing 5 mM CaCl$_2$, 0.05% Brij 35, and 0.02% NaN$_3$). The casein was $^{14}$C acetylated according to the method described in Cawston et al., above. The stromelysin activity in the presence of 1 mM, or a dilution thereof, was compared to activity in a control devoid of inhibitor and the results reported as that inhibitor concentration effecting 50% inhibition of the stromelysin (IC$_{50}$).

EXAMPLE C
Gelatinase inhibition activity

The potency of the compounds of general formula (I) to act as inhibitors of gelatinase was determined using the procedure of Harris and Krane ([1972] *Biochem. Biophys. Acta* 258:566–576), whereby a 1 mM solution of the inhibitor being tested or dilutions thereof was incubated at 37° C. for 16 hours with gelatinase and heat-denatured $^3$H or $^{14}$C-acetylated collagen (buffered with 50 mM Tris, pH 7.6, containing 5 mM CaCl$_2$, 0.05% Brij 35 and 0.02% NaN$_3$). The $^3$H or $^{14}$C gelatin was prepared by denaturing $^3$H or $^{14}$C—collagen produced according to the method of Cawston and Murphy, above, by incubation at 60° C. for 30 minutes. Undigested gelatin was precipitated by addition of trichloroacetic acid and centrifugation. The gelatinase activity in the presence of 1 mM, or dilution thereof, was compared to the activity in a control devoid of inhibitor and results reported as that inhibitor concentration effecting 50% inhibition of the gelatinase (IC$_{50}$).

EXAMPLE D
Inhibition of TNF-α production

The potency of the compounds of general formula (I) to act as inhibitors of the production of TNF-α was determined using the following procedure. A 1 mM solution of the inhibitor being tested or dilutions thereof was incubated at 37° C. in an atmosphere of 5% CO$_2$ with U937 cells (human histiosytic lymphoma) suspended in RPM1 1640 medium at a cell density of 2×10$^6$/ml and stimulated with 50 nM final concentration of PMA. After 18 hours, the supernatant is assayed for the levels of TNF-α using a commercially-available ELISA kit (R & D Systems). The activity in the presence of 1 mM inhibitor or dilutions thereof was compared to activity in a control devoid of inhibitor and results reported as that inhibitor concentration effecting 50% inhibition of the production of TNF-α.

Compounds of the invention have activity, measured by any or all of Examples A to D.

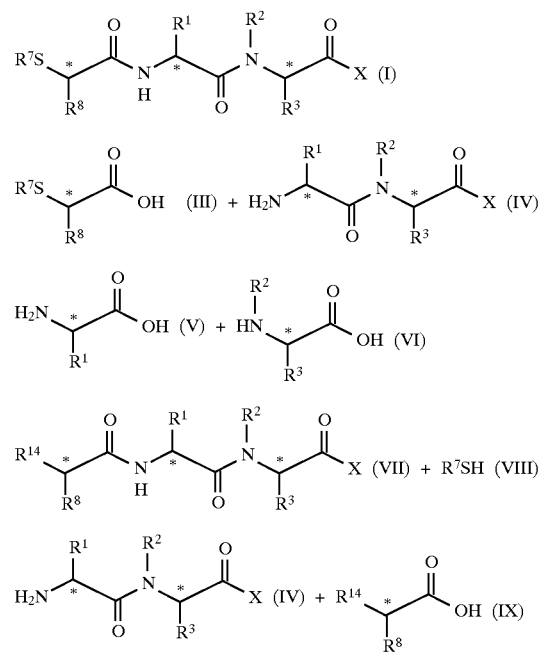

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound of formula I

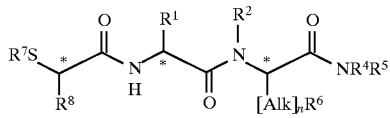

wherein
$R^1$ is $C_{2-6}$ alkyl, $C_{2-6}$ alkenyl, aryl, $(C_{1-6}$ alkyl)aryl or $C_{1-6}$ alkyl—$AR^9$ where A is O, $NR^9$ or $S(O)_m$, where m=0–2, and the or each $R^9$ is H, $C_{1-4}$ alkyl, aryl or $(C_{1-4}$ alkyl)aryl;

$R^2$ is H or $C_{1-6}$ alkyl;

either $R^4$ is H or $C_{1-6}$ alkyl optionally substituted by amino ($NH_2$), arylamino, protected amino, aryl, di($C_{1-6}$ alkyl)amino, mono($C_{1-6}$ alkyl)amino, $CO_2H$, protected carboxyl, carbamoyl, mono($C_{1-6}$ alkyl)carbamoyl or di($C_{1-6}$ alkyl)carbamoyl, and $R^5$ is H or $C_{1-6}$ alkyl, or $NR_4R_5$ is pyrrolidino, piperidino or morpholino;

$R^6$ is optionally-substituted $C_{3-6}$ cycloalkyl, $C_{3-6}$ cycloalkenyl, $C_{1-6}$ alkyl, benzyl, ($C_{1-6}$ alkoxy)benzyl, benzyloxybenzyl or 3-indolylmethyl;

Alk is $C_{1-6}$ alkyl or $C_{2-6}$ alkenyl and n=0 or 1;

$R^7$ is H or $R^{10}CO$ where $R^{10}$ is $C_{1-4}$ alkyl, $(C_{1-4}$ alkyl)aryl, $C_{3-6}$ cycloalkyl, $(C_{3-6}$ cycloalkyl)$C_{1-4}$ alkyl, $C_{2-6}$ alkenyl or $(C_{2-6}$ alkenyl)aryl;

$R^8$ is H, $C_{1-4}$ alkyl, $(C_{1-4}$ alkyl)aryl or aryl;

aryl is optionally-substituted phenyl or naphthyl, and the optional substituents are selected from halogen, $CF_3$, $C_{1-6}$ alkyl, alkoxy and phenyl;

or a salt, solvate or hydrate thereof.

2. The compound of claim 1, wherein $R^1$ is alkyl, alkenyl, aryl or alkylaryl; and $R^7$ and $R^8$ are each H.

3. The compound of claim 1, selected from the group consisting of

N-[N-(mercaptoacetyl)-L-leucyl]-L-phenylalanine methylamide;

N-(acetomercaptoacyl)-L-leucyl]-L-phenylalanine methylamide;

2-(Acetyltlio)pentanoyl-L-leucyl-L-phenylalanine N-methylamide;

2-(Acetylthio)propanoyl-L-leucyl-L-phenylalanine N-methylamide;

2-(Acetylthio)-3-methylbutanoyl-L-leucyl-L-phenylalanine N-methylamide;

2-(Acetylthio)-2-phenylacetyl-L-leucyl-L-phenylalanine N-methylamide;

2-(Acetylthio)-3-phenylpropanoyl-L-leucyl-L-phenylalanine N-methylamide;

2-(Acetylthio)-4-phenylbutanoyl-L-leucyl-L-phenylalanine N-methylamide;

N-(Acetylmercaptoacyl)-L-threonyl-L-phenylalanine methylamide;

N-(Acetylmercaptoacyl)-L-leucyl-L-tryptophan methylamide;

2-Mercaptopentanoyl-L-leucyl-L-phenylalanine N-methylamide;

2-Mercaptopropanoyl-L-leucyl-L-phenylalanine N-methylamide;

2-Mercapto-3-methylbutanoyl-L-leucyl-L-phenylalanine N-methylamide;

2-Mercapto-2-phenylacetyl-L-leucyl-L-phenylalanine N-methylamide;

2-Mercapto-3-phenylpropanoyl-L-leucyl-L-phenylalanine N-methylamide;

2-Mercapto-4-phenylbutanoyl-L-leucyl-L-phenylalanine N-methylamide;

N-[N-(Mercaptoacetyl)-L-threonyl]-L-phenylalanine methylamide; and

N-[N-(Mercaptoacetyl)-L-leucyl]-L-tryptophan methylamide.

4. The compound of claim 1, in the form of a single enantiomer or diastereomer, or a mixture of such isomers.

5. A pharmaceutical composition for use in therapy, comprising a compound of claim 1 and a physiologically-acceptable diluent or carrier.

6. A method for the prevention or treatment of a condition associated with matrix metalloproteinase or TNF activity, comprising administering an effective amount of the compound of claim 1 to a person in need of such treatment.

7. The method, according to claim 6, wherein said condition is selected from the group consisting of inflammation, fever, cardiovascular effects, haemorrhage, coagulation and acute phase response, cachexia and anorexia, acute infections, shock states, graft versus host reactions, autoimmune disease, malaria, reperfusion injury, meningitis, psoriasis, tissue breakdown, periodontitis and gingivitis.

8. The method, according to claim 6, wherein said condition is selected from the group consisting of tumours, tumour growth, angiogenesis and invasion by secondary metastases.

9. The method, according to claim 6, wherein said condition is selected from the group consisting of rheumatoid arthritis, osteoarthritis, bone resorption, or multiple sclerosis.

10. The method, according to claim 6, wherein said compound is administered in a physiologically-acceptable diluent or carrier.

* * * * *

UNITED STATES PATENT AND TRADEMARK OFFICE
CERTIFICATE OF CORRECTION

PATENT NO. : 5,853,623
DATED : December 29, 1998
INVENTOR(S) : John Montana, et al.

It is certified that error appears in the above-identified patent and that said Letters Patent is hereby corrected as shown below:

Column 21, line 40: "2-(Acetyltlio)" should read --2-(Acetylthio)--.

Signed and Sealed this

Seventh Day of September, 1999

Attest:

Q. TODD DICKINSON

Attesting Officer  Acting Commissioner of Patents and Trademarks